United States Patent
Weyl

(10) Patent No.: US 6,322,681 B1
(45) Date of Patent: Nov. 27, 2001

(54) GAS SENSOR

(75) Inventor: Helmut Weyl, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/362,613

(22) Filed: Jul. 28, 1999

(30) Foreign Application Priority Data

Jul. 28, 1998 (DE) .............................................. 198 33 861

(51) Int. Cl.$^7$ .................................................. G01N 27/407
(52) U.S. Cl. .......................... 204/424; 204/426; 204/428
(58) Field of Search ..................................... 204/421–429

(56) References Cited

U.S. PATENT DOCUMENTS

| | | | |
|---|---|---|---|
| 4,339,320 | * 7/1982 | Friese et al. ......................... | 204/428 |
| 4,915,815 | * 4/1990 | Shibata et al. ....................... | 204/428 |
| 5,246,562 | 9/1993 | Weyl et al. . | |
| 5,711,863 | * 1/1998 | Henklemann ........................ | 204/428 |
| 5,900,129 | * 5/1999 | Tsuji et al. ........................... | 204/424 |
| 5,948,963 | * 9/1999 | Kato et al. ........................... | 204/428 |
| 6,083,371 | * 7/2000 | Weyl et al. ........................... | 204/426 |

* cited by examiner

*Primary Examiner*—T. Tung
(74) *Attorney, Agent, or Firm*—Kenyon & Kenyon

(57) ABSTRACT

A gas sensor, in particular for determining the content of gases in the exhaust of an internal combustion engine, has a contact part carrier composed of two opposing, externally symmetrical half-shells, engaging in and contacting the terminal end of a sensor which runs axially and is installed in a tubular protective sleeve, with the half-shells of the contact part carrier being held together by a spring element. The spring element is designed to exert only a low clamping force on the half-shells of the contact part carrier in a first bracing step when the contact part carrier is pre-mounted on the terminal end of the sensor, so that the sensor can still be inserted easily between the two half-shells. In a second bracing step it presses from all sides against the two half-shells due to the inside wall of the protective sleeve and pushes them against the supporting contact points with a greater force than in the first bracing step.

8 Claims, 2 Drawing Sheets

GAS SENSOR

FIELD OF THE INVENTION

The present invention relates to a gas sensor, in particular for determining the content of gases in the exhaust of an internal combustion engine, with a contact part carrier composed of two opposing, externally symmetrical half-shells which engage in and make contact with the terminal end of a sensor which extends axially and is installed in a tubular protective sleeve, with the half-shells of the contact part carrier being held together by a spring element.

BACKGROUND INFORMATION

A gas sensor is known, for example, from German Patent Application No. 41 26 378. With the known design, two contact shells in which the electric contact parts are mechanically secured are pressed against the contact points of the sensor element by a horseshoe-shaped or hexagonal spring element which is open at one end. A spring element (spring clip) which is also clipped on it ensures the vibrational strength of this design. However, when more than six terminals are provided on the sensor, secure contact for all contact points is no longer guaranteed. In addition, the installation space would be too small due to the additional space required for the mechanical anchoring of the contacts.

SUMMARY OF THE INVENTION

An object of the present invention is to permit vibration-proof contacting that is thermally stable up to a temperature of 500° C. and is vibration-resistant up to 1300 m/s$^2$ for a gas sensor having at least seven terminals, with negligible contact resistance (in the nano-ohm range) so that a sufficiently great pressing force of the half-shells of the contact part carrier can be achieved with a single inexpensive spring element, while at the same time facilitating assembly of the contact part carrier.

The above-mentioned object is achieved according to the present invention with a gas sensor by designing the spring element so that it exerts only a low clamping force on the half-shells of the contact part carrier in an initial bracing step when the contact part carrier is pre-mounted on the terminal end of the sensor, so that the sensor can still be inserted easily between the two half-shells, and by the fact that in a second bracing step, it presses with a greater force from all sides against the half-shells, pressing them against the load-bearing contact points, than in the first bracing step through the inside wall of the protective sleeve.

The present invention is a combination of a soldered or welded connection and a clamped connection, with the actual contacting being achieved by the soldered or welded connection, but the mechanical load relief and short-circuit protection being provided by the half-shells of the contact part carrier.

The externally symmetrical half-shells of the contact part carrier are held together by the spring element designed according to the present invention, which exerts only a low clamping force on the half-shells in the first bracing step, so that the end of the sensor element with the contacts can still be inserted easily during assembly.

The protective sleeve may have a specific inside diameter which is adapted to the outside dimensions of the contact part carrier as well as the spring element pushed over it, so that the second bracing step is achieved on pushing the protective sleeve having a specific inside diameter onto it. As an alternative, the protective sleeve may have a circular caulking, so that this circular caulking causes a subsequent reduction in the inside diameter of the protective sleeve and thus produces the second bracing step.

This spring element is preferably a ring spring made of steel, which may come in various shapes, e.g., a helical spring with inclined windings such as that available under the brand name Bal Seal from Bal Seal Engineering Europe BV, Rhijnspoorplein 26, Amsterdam. As an alternative, the spring element may also be a spiral spring made of thin spring wire coiled up into a ring, which is slightly deformed into an oval when the outer protective sleeve is pushed over it. Additional spring elements may include U-shaped rings made of thin spring strips or star-shaped rings which are brought to their second bracing step either when the protective sleeve with a corresponding inside diameter is pushed onto them or by a subsequent reduction in the diameter of the protective sleeve, in particular by circular caulking.

As a result of this subsequent bracing step, the half-shells of the contact part carrier are exposed to a force acting symmetrically from all sides due to the design of the spring element according to the present invention, so that the contacts withstand the required vibrational load.

Due to subsequent setting processes during operation, which can be accelerated by a suitable design of the contact parts, the contacts which are not initially located in the magnetic flux are put under load, and thus the load on the soldered joints or welded joints is relieved when there are more than three contacts per side.

On the whole, the gas sensor designed according to the present invention has the following advantages:

- more than three contacts are possible per side of the sensor;
- a second additional clip spring can be omitted;
- extremely reliable contact behavior is achieved due to the combination of the soldered or welded joint with clamping by the spring element;
- the components used are inexpensive; and
- known manufacturing methods can be used for the most part.

DETAILED DESCRIPTION

Figure 1:
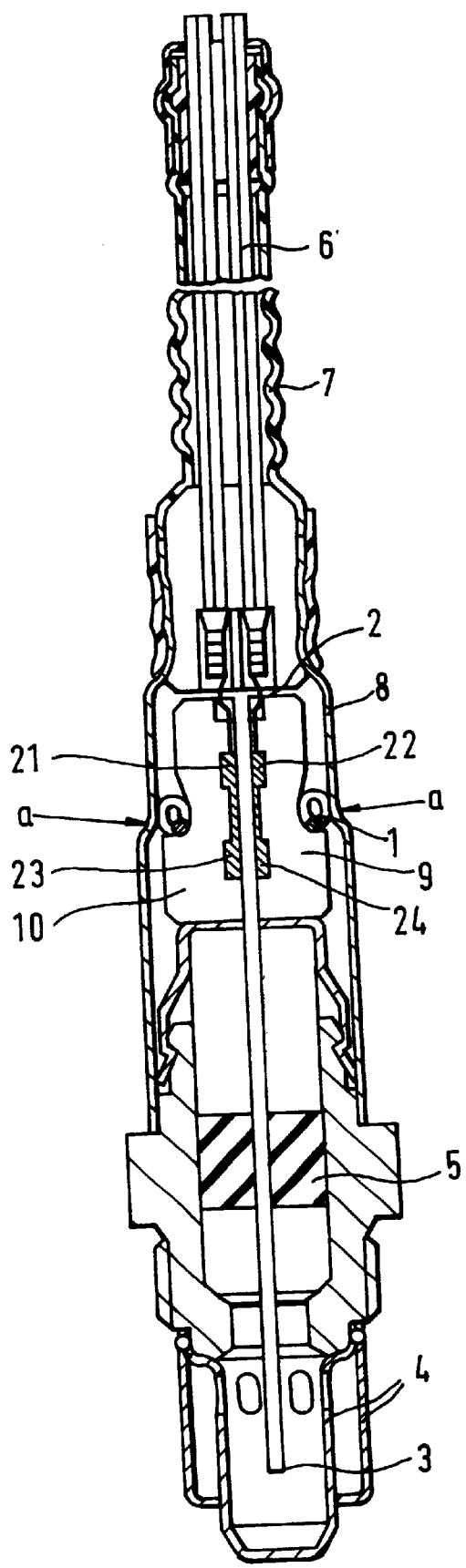
FIG. 1 shows a schematic longitudinal section through a gas sensor designed according to the present invention.

In the gas sensor designed according the present invention as shown in the schematic longitudinal diagram in FIG. 1, a sensor element 3 projects on the exhaust end into the interior of a double-walled protective tube 4 which is open for the exhaust gas to be determined. Toward the exhaust end, the interior of a reference gas space is sealed by a sealing package 5. On the terminal end of sensor element 3 there is a contact part carrier which has two symmetrical half-shells 9, 10 and has multiple contact parts, e.g., more than seven, with four contact parts 21–24 shown in FIG. 1. Toward the terminal end, these contact parts are designed in the form of contact clips 2 for solder terminals. Multiple terminal leads, preferably seven or more, are provided inside a flexible molded tubing 7 made of polytetrafluoroethylene (PTFE), for example.

The two half-shells 9, 10 of the contact part carrier are pressed together by a spring element 1 and by the section of a tubular protective sleeve 8 located there, so this design permits contacting that can resist temperatures of up to 500° C. and vibration up to 1300 m/s$^2$, and more than three contact parts are possible per side or per half-shell.

FIG. 1 shows that spring element 1 is deformed into a slightly oval shape due to the pressure exerted by the inside wall of protective sleeve 8, and thus it can exert a symmetrical and elastic compressive force on two half-shells 9 and 10. The contact paths (not shown in FIG. 1) on sensor 3 are contacted with contact parts 21–24 in the form of a combination of a soldered terminal or weld with a clamping joint, with the actual contacting being implemented by the soldered or welded connection, and with the mechanical relief and short-circuit prevention being achieved by the two half-shells 9 and 10 which are pressed together by spring element 1. Both half-shells 9 and 10 of the contact part carrier are preferably made of a ceramic material.

Figure 2:
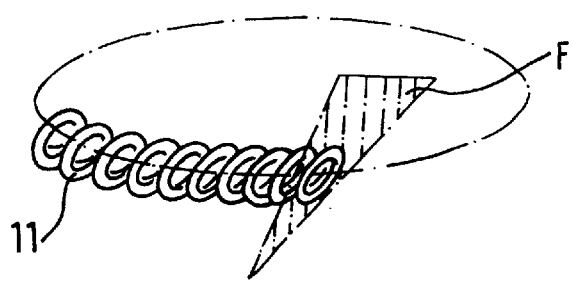
FIG. 2A shows a first alternative embodiment of a spring element which can be used with the gas sensor according to the present invention, as illustrated in FIG. 1.
FIG. 2B shows a second alternative embodiment of a spring element which can be used with the gas sensor according to the present invention, as illustrated in FIG. 1.
FIG. 2C shows a third alternative embodiment of a spring element which can be used with the gas sensor according to the present invention, as illustrated in FIG. 1.
FIG. 2D shows a fourth alternative embodiment of a spring element which can be used with the gas sensor according to the present invention, as illustrated in FIG. 1.
FIG. 2E shows a fifth alternative embodiment of a spring element which can be used with the gas sensor according to the present invention, as illustrated in FIG. 1.
Figure 2:
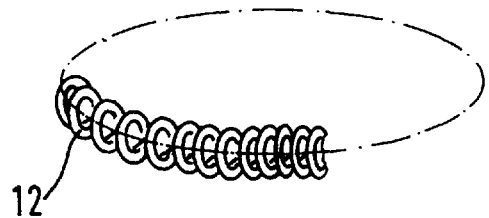
Figure 2:
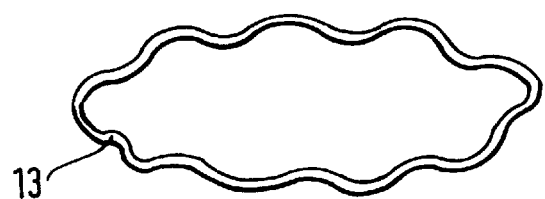
Figure 2:
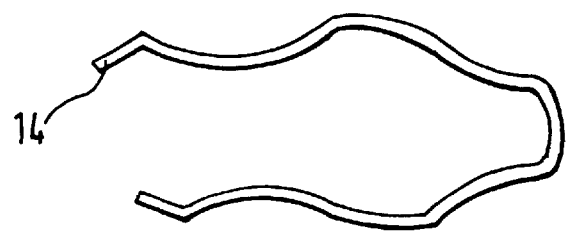
Figure 2:
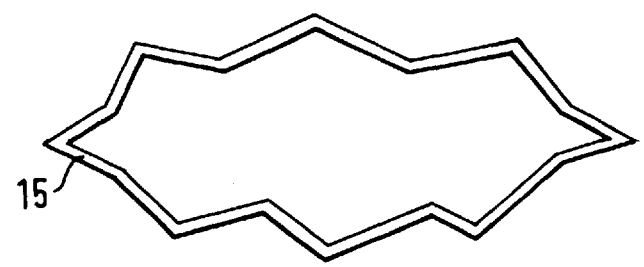

FIGS. 2A–2E show five different embodiments of a spring element 1 that can be inserted into the gas sensor according to FIG. 1. According to FIG. 2A, the spring element labeled with reference number 11 is designed in the form of a ring-shaped spring with inclined windings, such as that available from Bal Seal Engineering Europe BV. The elastic spring force of this ring spring becomes greater when the inclination of the windings becomes greater under increasing pressure. In FIG. 2A, an inclined face F represents the inclined position of the windings.

FIG. 2B shows a spring element 12 in the form of a helical spring made of thin spring wire coiled into a ring, its circular cross section being deformed in an oval shape under pressure, as indicated in FIG. 1.

FIG. 2C shows a spring element 13 in the form of a ring-shaped spring wire with corrugated deformation.

FIG. 2D shows a spring element 14 in the form of an open U-shaped ring made of a thin spring strip, while FIG. 2E shows a star-shaped spring ring.

The designs shown in FIGS. 2A–2E are implementations of a spring element 1, so that it exerts only a low clamping force on half-shells 9 and 10 of the contact part carrier in a first bracing step when the contact part carrier is pre-assembled on the terminal end of sensor 3, so that sensor 3 can still be inserted easily between two half-shells 9 and 10, and in a second bracing step a greater force is exerted from all sides, i.e., symmetrically, against the two half-shells 9 and 10, pressing them against the supporting contact points through the inside wall of protective sleeve 8.

The protective sleeve 8 may have a certain inside diameter, so that the second bracing step is achieved when protective sleeve 8 equipped with a certain inside diameter is pushed into position, or protective sleeve 8 may have a circular caulking, as represented by arrows a—a in FIG. 1, in the completely assembled state, so that the second bracing step is achieved due to the subsequent reduction in the inside diameter of protective sleeve 8 brought about by the circular caulking.

What is claimed is:

1. A gas sensor comprising:

a tubular protective sleeve having an inside wall;

a contact part carrier including two opposing, externally symmetrical half-shells;

a spring element for holding together the two half-shells; and a sensor extending axially and being installed with the contact part carrier and the spring element in the tubular protective sleeve, the sensor having a terminal end, the two half-shells of the contact part carrier engaging in and forming contact with the terminal end of the sensor at supporting contact points therein;

wherein the spring element exerts a low clamping force on the two half-shells when the contact part carrier is pre-mounted on the terminal end of the sensor such that the sensor is insertable between the two half-shells to form a pre-mounted assembly of the sensor, the two half-shells and the spring element, and wherein, when the pre-mounted assembly is installed in the protective sleeve, the spring element presses from all sides against the two half-shells through the inside wall of the protective sleeve, the spring element pushing the two half-shells towards each other and pushing the two half-shells against the supporting contact points with a greater force than the low clamping force.

2. The gas sensor according to claim 1, wherein the protective sleeve has a preselected inside diameter, the pre-mounted assembly being installed in the protective sleeve by mounting the protective sleeve onto the pre-mounted assembly.

3. The gas sensor according to claim 1, wherein the protective sleeve has a circular caulking in a finished assembled state, the circular caulking reducing an inside diameter of the protective sleeve when the pre-mounted assembly is installed in the protective sleeve.

4. The gas sensor according to claim 1, wherein the spring element includes a ring spring composed of steel.

5. The gas sensor according to claim 1, wherein the spring element includes a helical spring with inclined windings.

6. The gas sensor according to claim 1, wherein the spring element includes a spiral spring composed of a thin spring wire coiled into a ring shape.

7. The gas sensor according to claim 1, wherein the spring element forms a star-shaped ring.

8. The gas sensor according to claim 1, wherein the spring element includes an open U-shaped ring composed of a thin spring steel.

* * * * *